United States Patent [19]
Kleinberg et al.

[11] Patent Number: 5,642,220
[45] Date of Patent: Jun. 24, 1997

[54] MICROSCOPE BALANCE COMPENSATOR

[76] Inventors: Larry K. Kleinberg, 16322 Peppermill Dr., St. Louis, Mo. 63005; Gerald S. Gahn, 417 Arbor Meadow Ct., St. Louis, Mo. 63021

[21] Appl. No.: 307,361

[22] Filed: Sep. 16, 1994

[51] Int. Cl.⁶ .................................................. G02B 21/00
[52] U.S. Cl. ........................... 359/384; 359/368; 359/382
[58] Field of Search ................................. 359/368, 382, 359/384, 391, 862, 377; 248/281.11, 280.11, 123.11, 585, 660, 325, 571; 192/88 B, 103 F, 104 B, 105 CF, 106 F

[56] References Cited

U.S. PATENT DOCUMENTS

| | | | |
|---|---|---|---|
| 4,668,057 | 5/1987 | Kleinberg | 359/381 |
| 4,742,947 | 5/1988 | Coffman et al. | 359/383 |
| 4,815,832 | 3/1989 | Nagano et al. | 359/388 |
| 4,867,405 | 9/1989 | Nakamura | 248/281.11 |
| 5,173,802 | 12/1992 | Heller | 359/384 |
| 5,186,422 | 2/1993 | Nakamura | 248/123.11 |

*Primary Examiner*—Thong Nguyen

[57] ABSTRACT

An apparatus for providing counteracting force to overcome the off-center weight of a microscope assembly without counterweights. The apparatus is a microscope balance compensator which uses springs or gas pistons to compensate for a change in a moment developed in a microscope assembly when attachments are added or removed or when the tilt angle of the microscope is changed. The microscope balance compensator includes one device for applying counteracting force about a tilt axis and another device for applying counteracting force about a tip axis oriented perpendicular to the tilt axis. Each counteracting force is applied at discrete angles relative to the pivot centers and is adjustable. The apparatus provides balance compensation over a wide range without adding counterweight, thereby minimizing the total weight of the microscope.

20 Claims, 11 Drawing Sheets

SYSTEM TORQUE = WL SIN α

ROTATION ANGLE (α)

β - PHASE SHIFT DUE TO ADDED WEIGHT (W₂)

MICROSCOPE BALANCE COMPENSATOR

FIELD OF THE INVENTION

This invention relates to microscope assemblies in which the microscope can be tilted and tipped about mutually perpendicular rotational axes. In particular, the invention relates to mechanisms for compensating unbalanced moments about these rotational axes when attachments are added to or removed from a microscope assembly.

BACKGROUND OF THE INVENTION

Surgical procedures for the treatment of patient tissue frequently require visual contact by the surgeon with a target area which is limited in size. In the field of microsurgery, a surgical operation is performed while the surgeon and his assistants simultaneously view the target area by way of respective binoculars optically coupled to the microscope along respective optical paths. These binoculars provide the surgeon and the observers with the same view of the targeted tissue.

During surgical procedures, the surgeon must move the microscope as needed to optimize his view of the tissue being treated. At different stages of the procedure, the surgeon will need to view the subject tissue from different observation angles. Accordingly, the microscope must be easily manipulatable during the procedure to allow the surgeon to accurately direct and focus the microscope at the particular area of interest. Such manipulations must be performed rapidly in order to minimize any delay in carrying out the surgical procedure. Furthermore, the surgical microscope must be supported on a stand or suspended from a ceiling support in a manner that allows the microscope to be manipulated into a desired position within a working space without any obstruction to the surgical procedure.

In addition, it is desirable that the microscope assembly be adaptable for use in different surgical disciplines without the need for tools to convert the microscope from one physical assembly to another. The need to reconfigure the assembly using tools requires that doctors, nurses or other technical personnel be trained. Such training is an added burden in terms of time, cost and effort to hospitals and medical centers. Therefore, a versatile surgical microscope in which the relative positions of various components can be changed and adjusted to meet the requirements of different disciplines, e.g., otolaryngology versus ophthalmology, is preferred.

One conventional surgical microscope assembly includes the following: a microscope; a housing or casing by means of which one or more observer's tube assemblies can be mounted to the assembly; an illumination module which changes the magnification of the object or target area visible through the binoculars of the microscope (and observer's tube assembly); a fiber optics cable which transmits light to the illumination module; a mechanical assembly for changing the tilt of the microscope; means for focusing the microscope; and an adjustable tilt-axis counterweight to balance the assembly. A second adjustable counterweight is provided to prevent lateral or transverse tip of the assembly of elements when one or more laterally extending accessories (e.g., an observer's tube assembly) are added or removed. The microscope assembly optionally includes a video path to allow the microsurgery to be recorded by a video camera.

All of these elements are mounted on a support arm coupled to a mounting member. The support arm is mounted to a mounting member suitably connected to a ceiling, wall or other counterweight stand, either directly or through an angle coupling. The support arm's position is swingable through a 180° arc about the axis of the mounting member. Further, the means for mounting the microscope on the support arm is rotatable about a tilt axis extending through the mechanical assembly.

With each attachment or accessory which is incorporated as part of the assembly, the microscope assembly increases in weight. This increased weight impairs the surgeon's ability to maneuver the microscope easily and accurately. Thus, it is desirable to minimize the weight of the microscope assembly. In particular, it would be advantageous to provide a mechanism for counterbalancing a change in a moment developed about the tilt or tip axis which did not require the use of counterweights.

SUMMARY OF THE INVENTION

The present invention is an apparatus for providing counteracting force to overcome the off-center weight of the microscope assembly without using counterweights. The apparatus is a microscope balance compensator which uses springs or gas pistons to compensate for a change in a moment developed about either the tip axis or the tilt axis in a microscope assembly when attachments are added or removed or in a moment developed about the tilt axis when the tilt angle of the microscope is deliberately changed. The microscope balance compensator includes one device for applying counteracting force about a tilt axis and another device for applying counteracting force about a tip axis. Each counteracting force is applied at discrete angles relative to the pivot centers and is adjustable. The apparatus provides balance compensation over a wide range without adding counterweight, thereby minimizing the total weight of the microscope. The balance compensator can be retrofitted to surgical microscopes to ensure precise two-axis balance without added clamp tension or counter-weight.

In accordance with the preferred embodiment of the invention, the moment exerted on the system by the spring/gas piston mechanism is approximately equal in magnitude but opposite in direction to the moment exerted on the system due to the weight of the microscope. This approximate balance can be maintained throughout the entire operating range of the system by simple manual adjustments. In particular, the invention provides a method of quickly adjusting for a change of off-center load for a limitless combination of accessories. This is accomplished by adjusting the phase angle of the torque versus rotation angle relationship to compensate for the phase shift about the tip axis of the system center of gravity produced by attachment or removal of an accessory.

The spring/gas piston arrangement of the invention compensates for the additional weight of the various combinations of accessories without adding counterbalance weight to the system. The spring/gas piston arrangement compensates for an off-center load on either side of its equilibrium position. As the center of gravity of the microscope passes through its equilibrium position, the moment due to the weight changes direction and the magnitude of the moment changes in proportion to the angle subtended from equilibrium. The moment exerted by the spring/gas piston also changes direction at the equilibrium position and the magnitude of the moment changes as a function of the angle subtended from equilibrium. This relationship is critical to provide the correct counterbalancing moment throughout the full operating range of the system.

A further aspect of the present invention is that the suspension points are positioned discretely with respect to the rotational axis, providing the necessary relationship between the system and the counterbalance moment. In addition, the invention provides for controlled repositioning of the suspension points to achieve an equality between the compensation moment and the moment due to system weight. This feature allows for variations in the relative positioning between the equilibrium position and the vertical axis of the microscope that occurs with different combinations of accessories. This provides a user-adjustable means for optimizing the counterbalance system throughout the entire operating range for any combination of accessories.

Finally, the invention automatically compensates for a change in the center of gravity normally encountered with a change in the fine focus of the microscope.

DETAILED DESCRIPTION OF THE PREFERRED EMBODIMENTS

Figure 1:
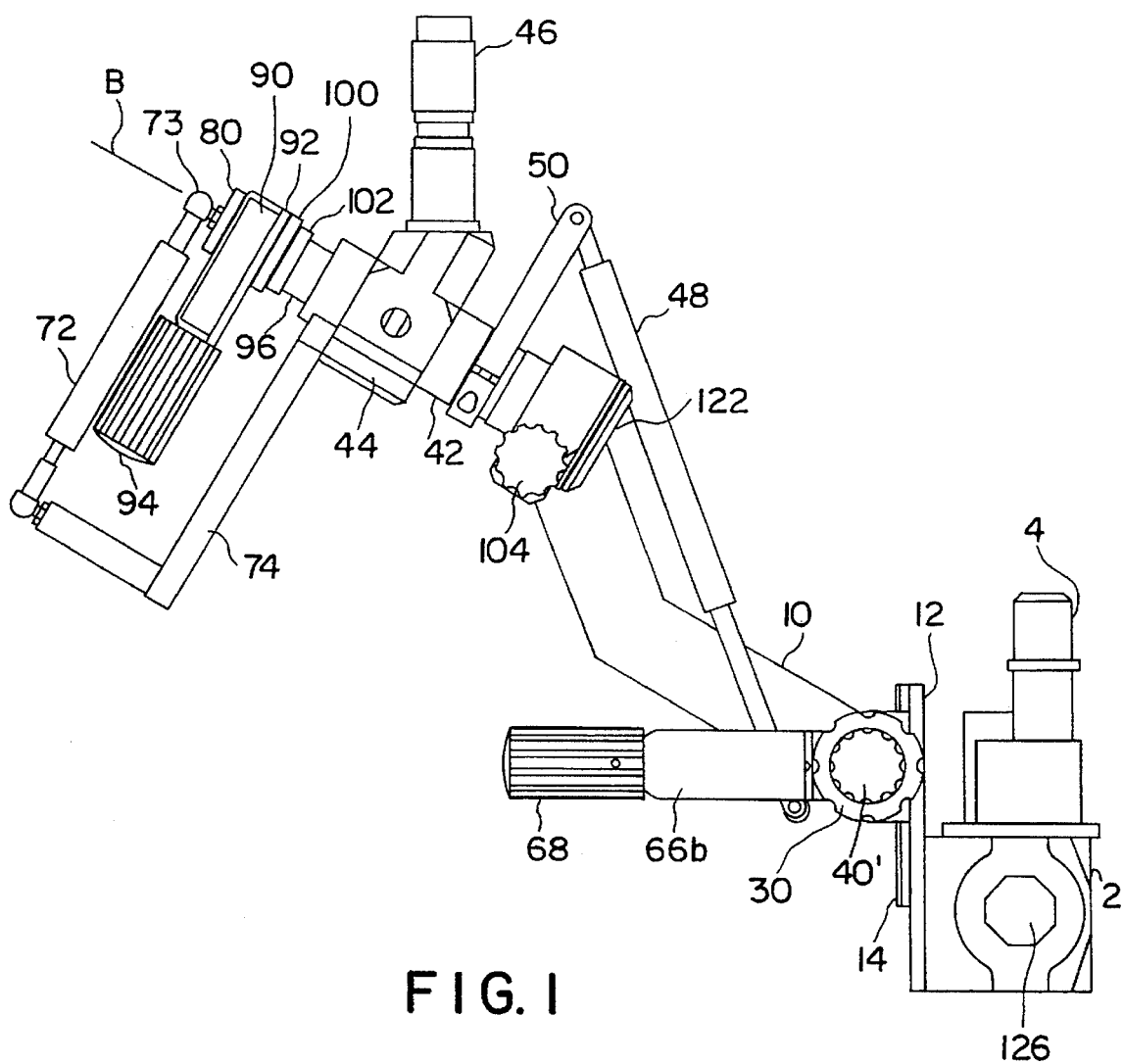
FIGS. 1 and 2 are side elevational views of a microscope assembly incorporating a microscope balance compensator in accordance with a preferred embodiment of the present invention, with the microscope oriented at first and second tilt positions respectively.

A microscope assembly incorporating a microscope balance compensator in accordance with a preferred embodiment of the present invention will be generally described with reference to FIGS. 1-4.

The microscope assembly shown in FIGS. 1-4 includes a microscope comprising a microscope housing 2 and binoculars 4. The microscope housing 2 is slidably mounted to a mounting block 6 to allow focusing of the microscope in response to rotation of focus adjustment knobs 40 and 40'. The mounting block 6 is rotatably mounted in one end of a support arm 10 with an axis of rotation A (hereinafter referred to as the tilt axis).

Figure 10:
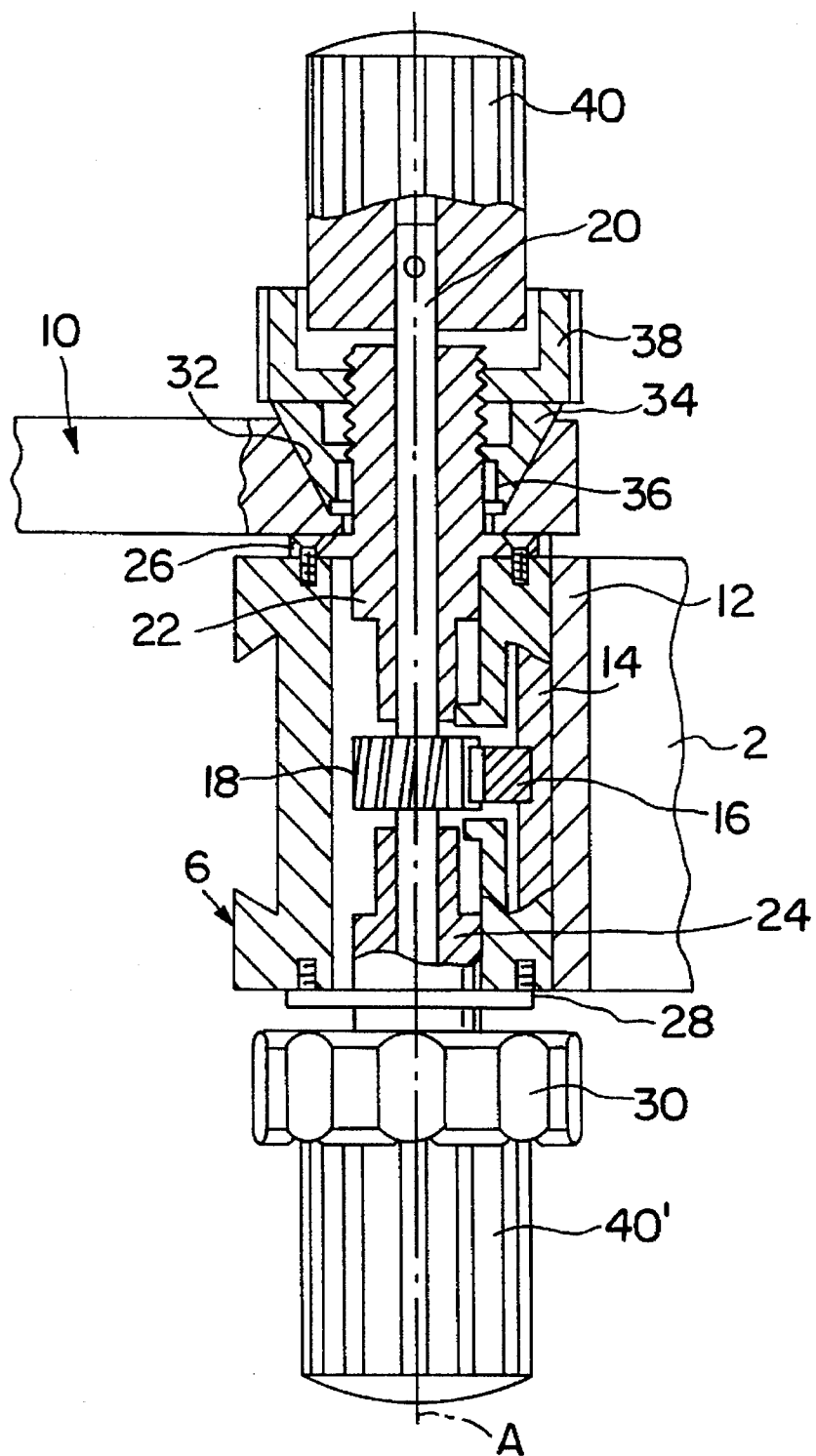
FIG. 10 is a cross-sectional view of a conventional mechanical assembly for enabling tilting and focusing of the microscope.

The various couplings between the focus adjustment knobs, the mounting block, the microscope housing and the support arm involve conventional structures of the type depicted in FIG. 10. The microscope housing 2 is secured to a plate member 12, which is slidably mounted on mounting block 6 via a conventional dovetail mount. Plate member 12 comprises a tongue 14 which fits slidably in a complementary groove formed in mounting block 6. Tongue 14 has a mitered rack member 16 secured thereto which cooperates with a pinion gear 18 suitably secured to a rotatable shaft 20 having focus adjustment knobs 40 and 40' mounted on the ends thereof. The shaft 20 is rotatably supported by a pair of spaced bearings or bushings 22 and 24 having annular portions 26 and 28, respectively, between and to which the mounting block 6 is secured. In response to rotation of the focus adjustment knobs 40 and 40', the plate member 12 can be raised or lowered as necessary to focus the microscope.

Rotation of knobs 40 and 40' is blocked by a clutch braking assembly (not shown) of the type described in U.S. Pat. No. 4,668,057 to Kleinberg, the disclosure of which is specifically incorporated by reference herein. An annular ring 30 is threadably coupled (not shown) to bushing 24, which incorporates the aforementioned clutch braking assembly. The annular ring 30 cooperates with the clutch braking assembly in a manner such that shaft 20 cannot be rotated when ring 30 is tightened and can be rotated when ring 30 is loosened.

The bushing 22 extends through a tapered hole 32 adjacent one end of the support arm 10, while a frustum member 34 mounts bushing 22, being keyed thereto as at 36, and being disposed in tapered hole 32 for complementary abutment to the latter's taper. An annular ring 38 is threaded to bushing 22 for abutment and adjustment relative to frustum member 34. Tightening of ring 38 against frustum member 34 causes frictional gripping thereof with support arm 10, thus stationarily positioning mounting block 6 relative to the support arm. Full loosening of ring 38 provides universal rotation mounting block 6 relative to support arm 10, enabling the microscope housing 2 to be tilted about tilt axis A. For example, in FIG. 2, the microscope is tilted by about 45° relative to the microscope position shown in FIG. 1.

Figure 2:
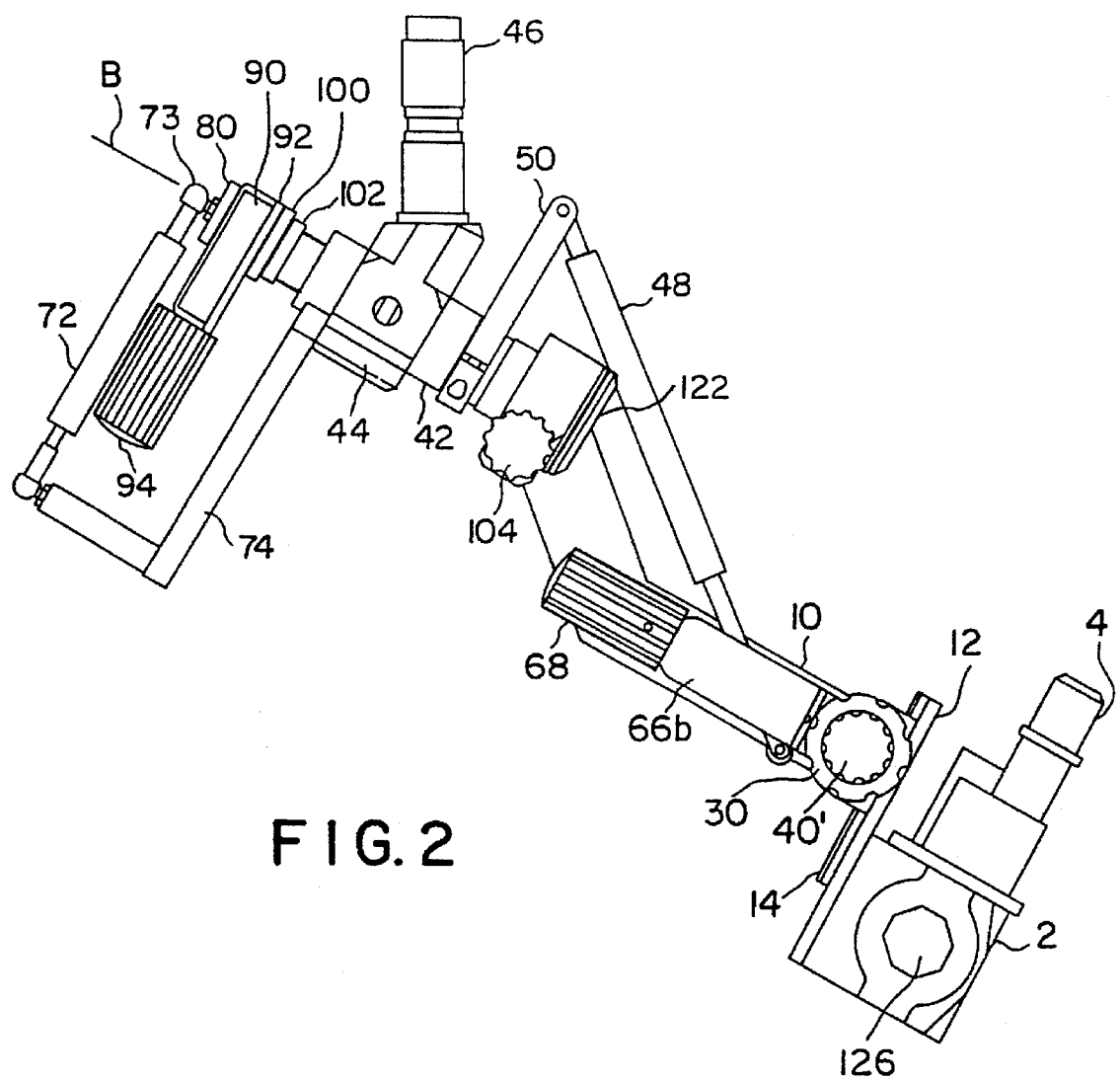

As best seen in FIGS. 1 and 2, the end of support arm 10 remote from the microscope is rigidly connected to a mounting post 42, which is in turn rotatably supported by a coupler 44. Mounting post 42 is rotatable about an axis of rotation B (hereinafter referred to as the tip axis). The coupler 44 is in turn rotatably mounted on the end of a mounting post 46, which may, for example, be suspended from a ceiling.

In accordance with the preferred embodiment of the present invention, a tilt axis gas piston 48 is positioned to apply a moment about tilt axis A to counteract the moment due to the weight of the microscope. The tilt axis gas piston 48 comprises a pressure tube having its free end pivotably coupled to an upper tilt axis piston mount 50 via a link 49 (see FIGS. 1–4) and a piston rod having its free end pivotably coupled to a lower tilt axis piston mount 52 (see FIGS. 7 and 8). The upper tilt axis piston mount 50 is rigidly secured to the mounting post 42.

Figure 3:
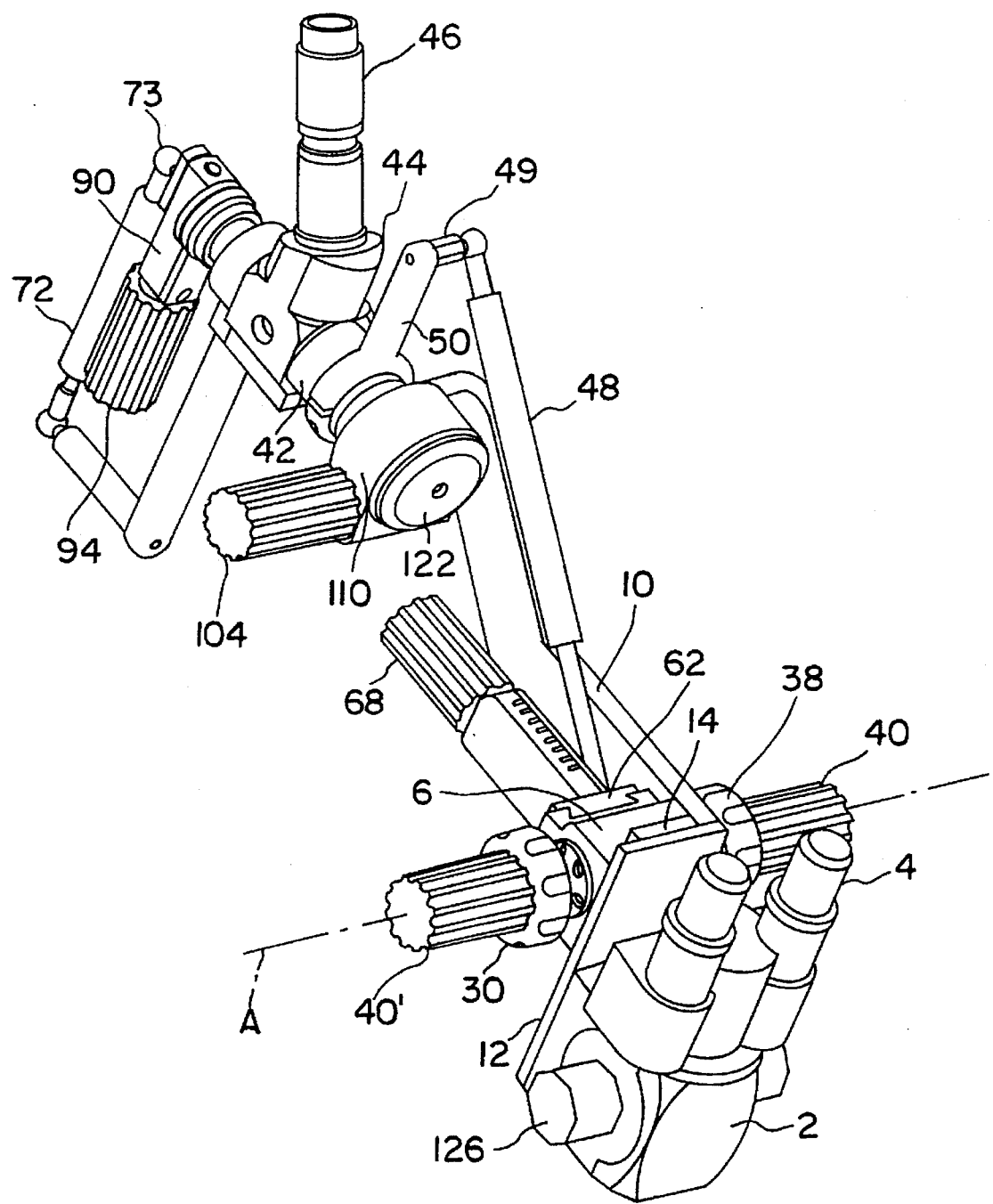
FIGS. 3 and 4 are isometric views, taken from respective viewing angles, of the microscope assembly shown in FIGS. 1 and 2.
Figure 4:
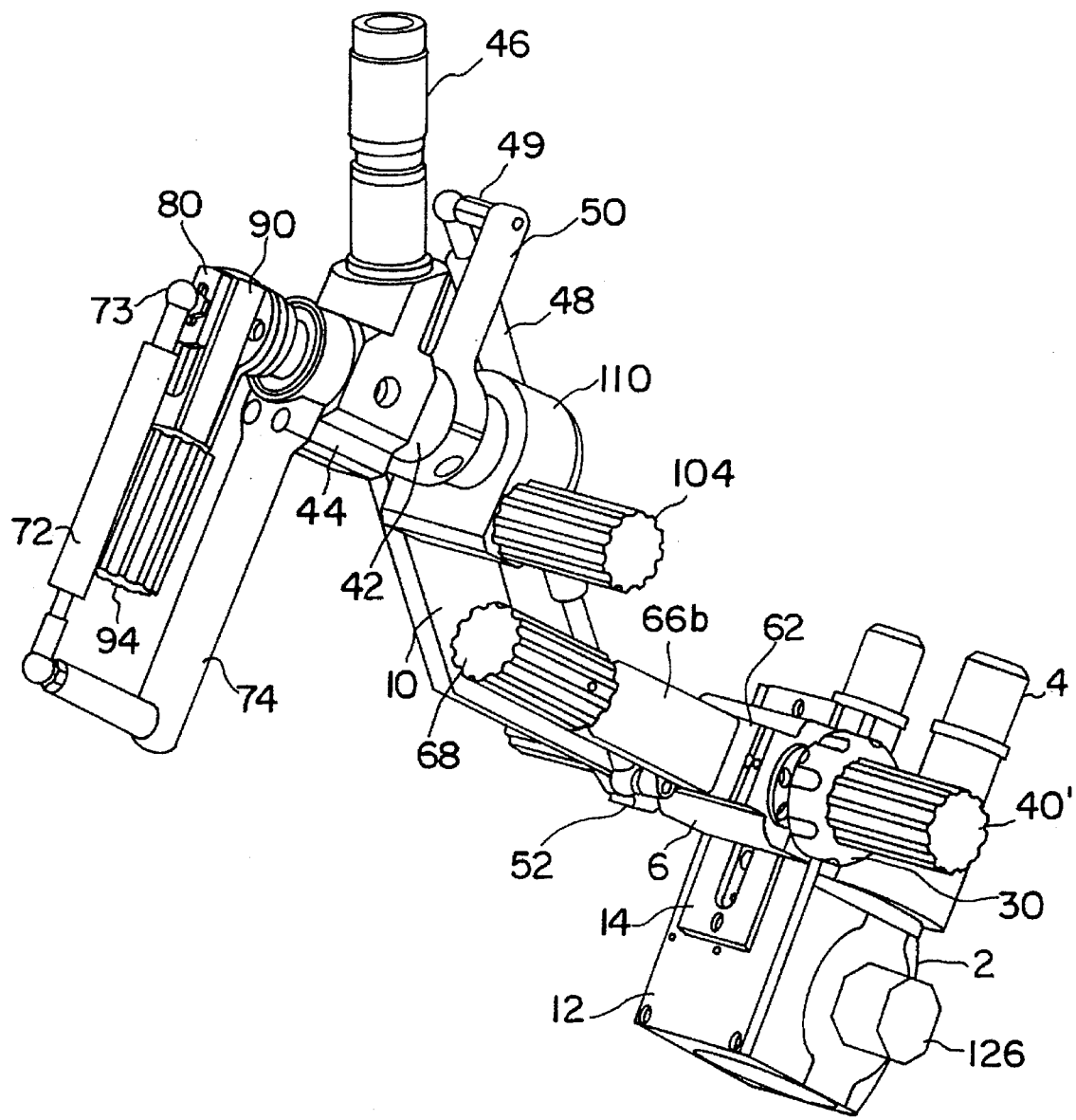
Figure 7:
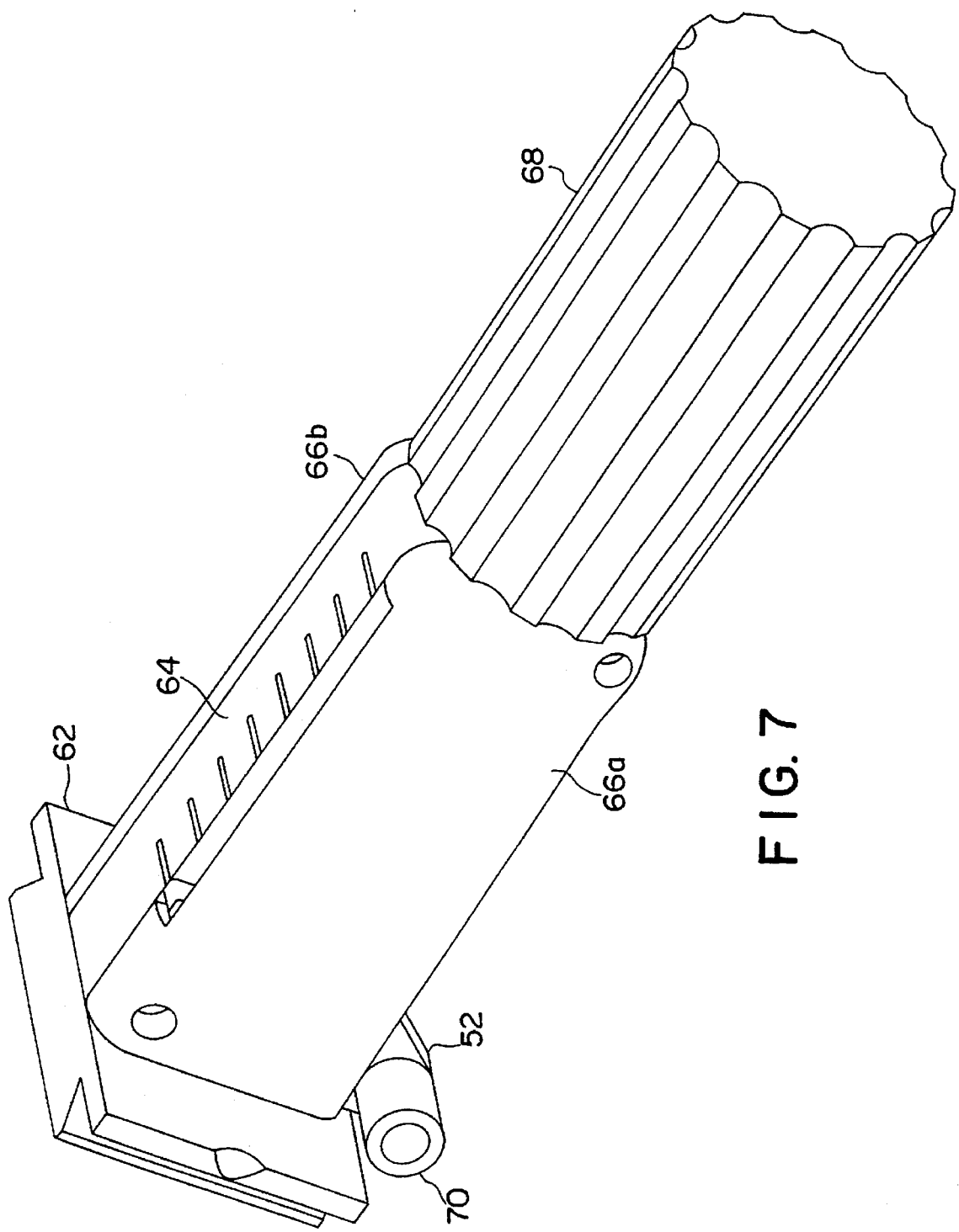
FIG. 7 is an isometric view of the counterbalance assembly for the tilt axis in accordance with the preferred embodiment of the invention.
Figure 8:
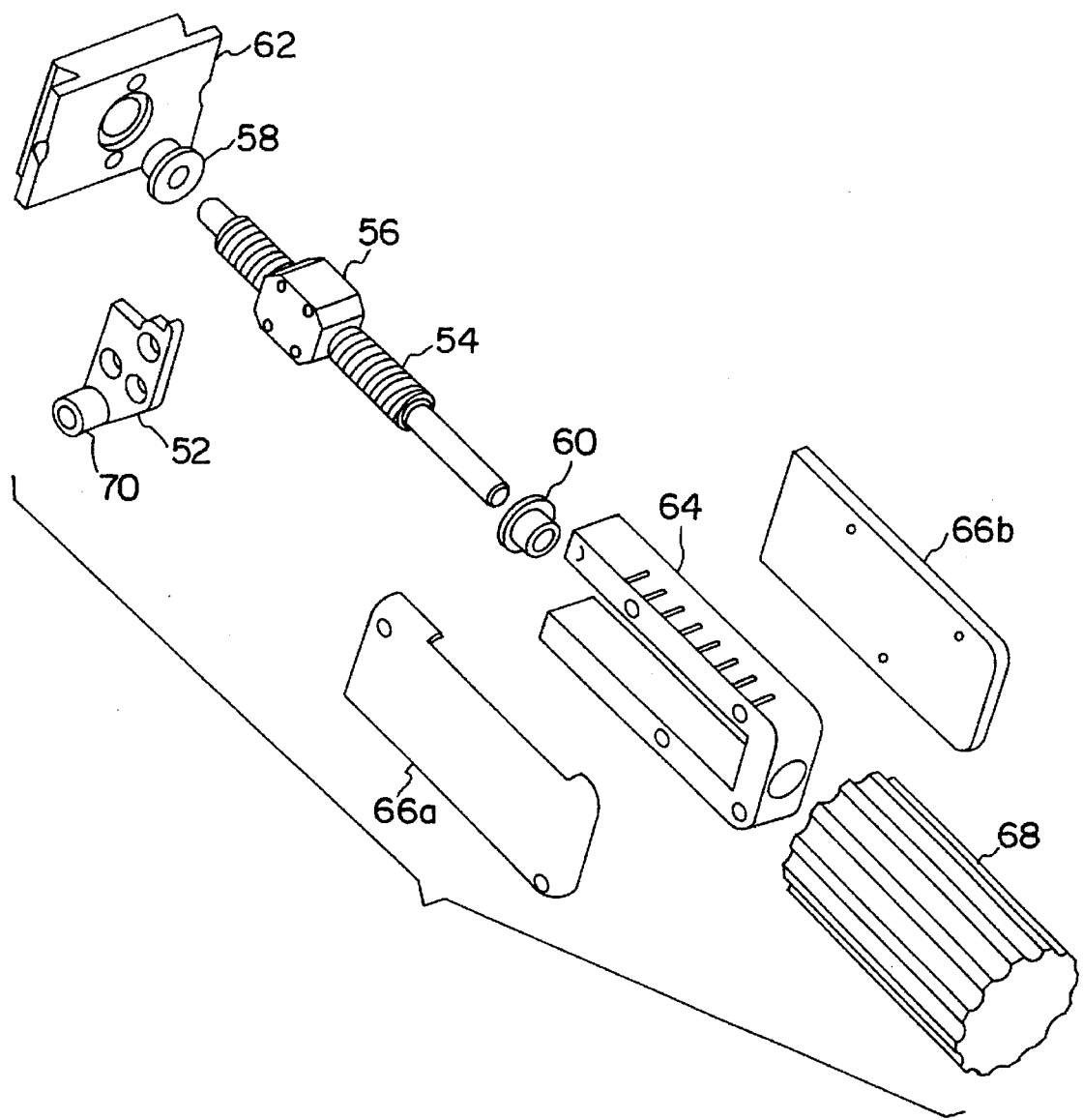
FIG. 8 is an exploded view of the counterbalance assembly for the tilt axis in accordance with the preferred embodiment of the invention.

The moment applied by the tilt axis gas piston 48 can be adjusted using the tilt axis counterbalance assembly shown in FIGS. 7 and 8. The tilt axis counterbalance assembly comprises a piston mount lead screw 54 on which a piston mount slide 56 is threadably mounted. The lower tilt axis piston mount 52 is secured to the piston mount slide 56. The piston mount lead screw 54 is rotatably supported at its respective ends by flange bearings 58 and 60. Flange bearing 58 resides in a bore having an annular seat which is formed in a dovetail mount 62. The dovetail mount 62 fits in a complementary groove in the mounting block 6, as best seen in FIG. 3. A U-shaped housing 64 has a bore with an annular seat for receiving the flange bearing 60. Housing 64 is closed on both sides by covers 66a and 66b. The ends of the legs of the U-shaped housing 64 are bolted to the dovetail mount 62, by means of which the tilt axis counterbalance assembly is rigidly coupled to the mounting block 6 for tilting in unison with the microscope.

A tilt axis torque adjustment knob 68 is secured to the protruding end of piston mount lead screw 54. In response to rotation of tilt axis torque adjustment knob 68, piston mount lead screw 54 is rotated. Since rotation of the piston mount slide 56 is blocked by the legs of U-shaped housing 64, piston mount slide 56 will translate as tilt axis torque adjustment knob 68 is rotated, carrying the lower tilt axis piston mount 52 with it. The pivot 70 of lower tilt axis piston mount 52 is arranged such that tilt axis gas piston 48 always exerts a moment about tilt axis A which opposes the moment due to the weight of the microscope and any attachments thereon. The gas piston 48 produces a moment urging an upper pivot 73 and the pivot 70 in opposite directions. The magnitude of that counteracting moment can be varied by rotating the tilt axis torque adjustment knob 68, which causes the pivot 70 to displace relative to tilt axis A, thus changing the moment developed via the torque applied by the tilt axis gas piston 48.

In accordance with a further feature of the present invention, a tip axis gas piston 72 is moved to an equilibrium position whereat the piston exerts a moment about tip axis B to counteract the off-center weight of the microscope assembly when accessories are attached. The moment applied by the piston 72 is adjustable by a counterbalance assembly. In particular, the magnitude of the moment applied about the tip axis is adjustable to produce a zero phase shift in response to a shift in the center of gravity of the microscope assembly due to the coupling/uncoupling of an accessory. The tip axis gas piston 72 comprises a pressure tube having its free end pivotably coupled to an L-shaped lower tip axis piston mount 74 (see FIGS. 1–4) and a piston rod having its free end pivotably coupled to a piston mount slide 76 (see FIGS. 5 and 6). The lower tip axis piston mount 74 is rigidly secured to the coupler 44.

Figure 5:
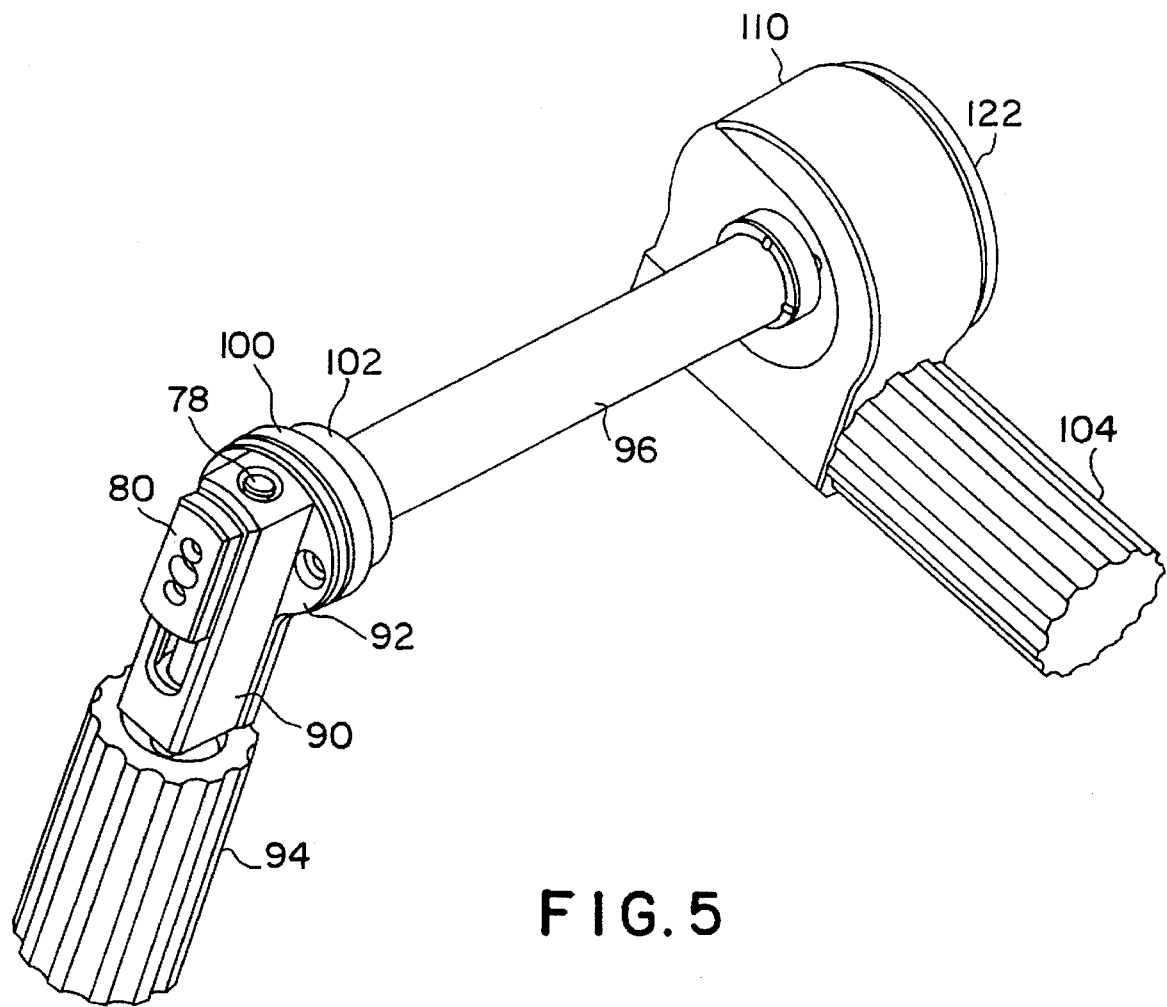
FIG. 5 is an isometric view of the counterbalance assembly for the tip axis in accordance with the preferred embodiment of the invention.
Figure 6:
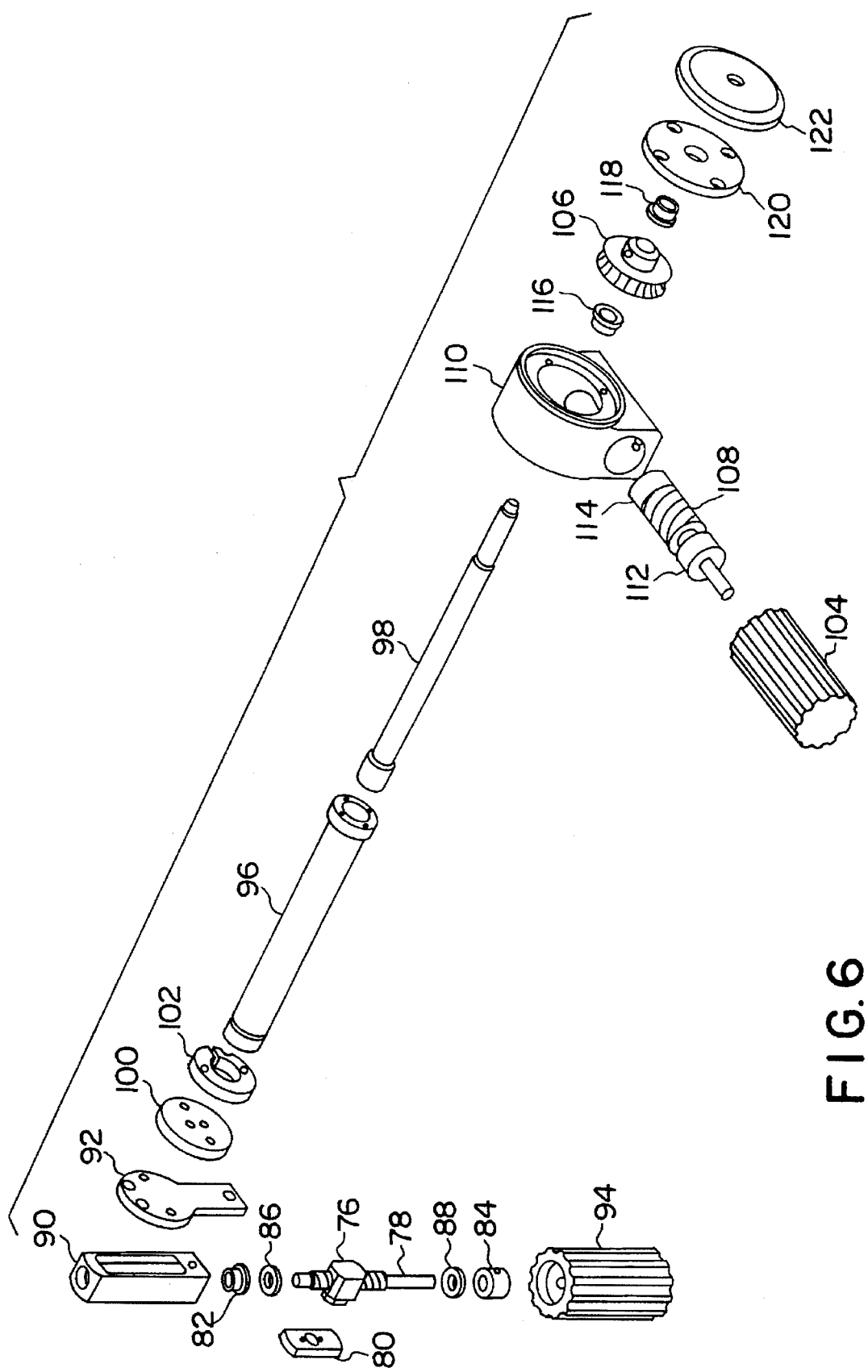
FIG. 6 is an exploded view of the counterbalance assembly for the tip axis in accordance with the preferred embodiment of the invention.

The moment applied by the tip axis gas piston 72 can be adjusted using the tip axis counterbalance assembly shown in FIGS. 5 and 6. The tip axis counterbalance assembly comprises a piston mount lead screw 78 on which piston mount slide 76 is threadably mounted. The gas piston 72 is pivotably coupled to the piston mount slide 76 with a bezel 80 therebetween. The piston mount lead screw 78 is rotatably supported at one end by a flange bearing 82 and at the other end by a retainer 84. Thrust washers 86 and 88 are respectively installed in abutment with the ends of flange bearing 82 and retainer 84 which face the piston mount slide 76. Flange bearing 82 resides in a bore having an annular seat which is formed in one end of a housing 90. The retainer 84 resides in a bore formed in the other end of housing 90. The housing 90 is mounted securely on a housing mounting plate 92.

A tip axis torque adjustment knob 94 is secured to the protruding end of piston mount lead screw 78. In response to rotation of tip axis torque adjustment knob 4, piston mount lead screw 78 is rotated. Since rotation of the piston mount slide 76 is blocked by the walls of housing 90, piston mount slide 76 will translate as tip axis torque adjustment knob 94 is rotated, carrying the upper pivot 73 of the tip axis gas piston 72 with it. At the upper limit of the sliding range of piston mount slide 76, the upper pivot 73 of the tip axis gas piston 72 occupies a position coaxial with the tip axis B.

Figure 11A:
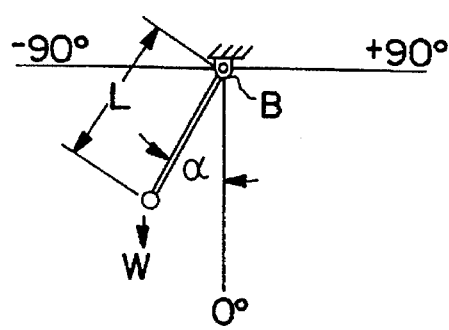
FIG. 11A is a schematic diagram of a symmetrically loaded microscope system of weight W which is rotatable about a tip axis B.
Figure 11B:
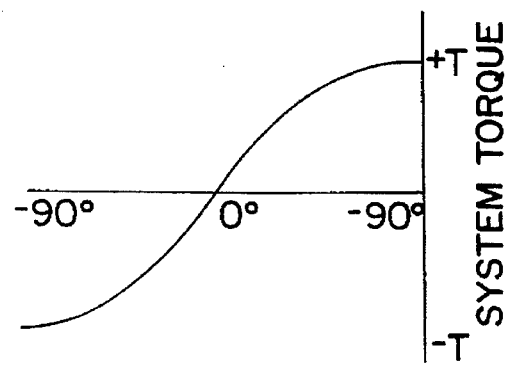
FIG. 11B is a graph showing the system torque versus rotation angle $\alpha$ relationship for the rotated microscope system diagrammed in FIG. 11A.
Figure 12A:
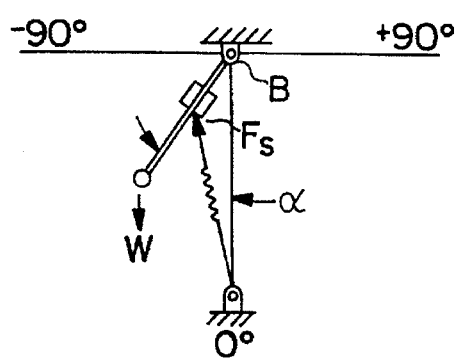
FIG. 12A is a schematic diagram of a symmetrically loaded microscope system of weight W which is rotatable about a tip axis B and which is coupled to a spring counterbalance which exerts a force $F_s$.
Figure 12B:
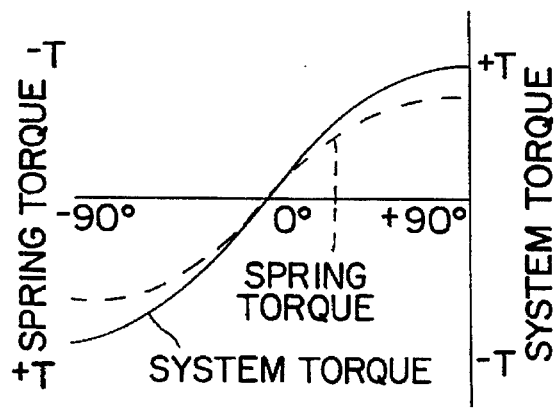
FIG. 12B is a graph showing the system torque and spring torque versus rotation angle $\alpha$ relationships for the rotated microscope system diagrammed in FIG. 12A.
Figure 13A:
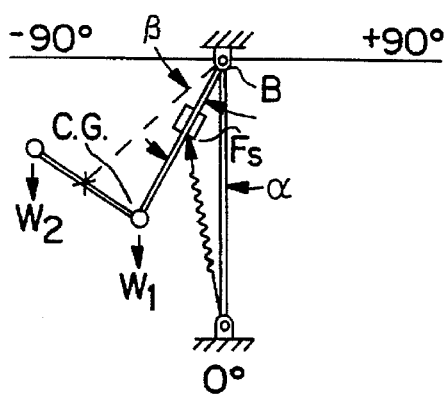
FIG. 13A is a schematic diagram of a asymmetrically loaded microscope system of weight $W_1$ which is rotatable about a tip axis B and which is coupled to a spring counterbalance which exerts a force $F_s$, the asymmetrical loading being due to the addition of an accessory of weight $W_2$.
Figure 13B:
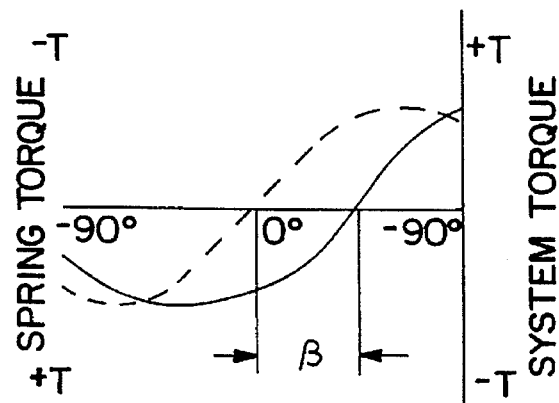
FIG. 13B is a graph showing the phase shift of the system torque relative to the spring torque due to the shift in center of gravity by an angle $\beta$ when weight $w_2$ is added to the system.

In accordance with the invention, the tip axis counterbalance assembly provides a method of quickly adjusting for a change of off-center load for a limitless combination of accessories which can be attached to the microscope. This is accomplished by adjusting the phase angle of the torque versus rotation angle relationship to compensate for the phase shift about the tip axis of the system center of gravity produced by attachment or removal of an accessory. FIG. 11A shows the weight W at the center of gravity when the microscope assembly is symmetrically loaded. FIG. 11B shows how the system torque varies with change in the tip axis rotation angle $\alpha$. FIG. 12A shows the weight W at the center of gravity of a symmetrically loaded microscope assembly which has a tip axis counterbalance spring. FIG. 11B shows how the system and spring torque vary with change in the tip axis rotation angle $\alpha$ under these conditions. As is evident from FIG. 12B, the system and spring torques are in phase. However, when the microscope assembly is asymmetrically loaded due, for example, to the attachment of an accessory having a weight $W_2$, as depicted in FIG. 13A, the center of gravity of the microscope assembly shifts by an angle $\beta$ and the system and spring torques become out of phase by the same angle (see FIG. 13B). The present invention solves this problem by incorporating a phase adjustment subassembly in the tip axis counterbalance assembly depicted in FIGS. 5 and 6. The function of that phase adjustment assembly is to allow the rotation of the piston mount slide 76 relative to the microscope assembly to create a phase shift of zero, thus providing the required balance for the system. Without this feature, the offset load cannot be balanced through a small ($\pm 45°$) rotation angle $\alpha$, as desired.

The phase adjustment subassembly is designed to be retrofitted in existing microscope assemblies having a mounting post rotatably supported by a coupler. Such retrofitting is accomplished by installing a phase adjustment tube 96 inside the mounting post 42. Phase adjustment tube 96 must be rigidly secured to mounting post 42 by any conventional means. A phase adjustment shaft 98 is rotatably supported inside of phase adjustment tube 96. The housing 90 is securely mounted on one end of phase adjustment shaft 98 by means of housing mounting plate 92, a mounting flange 100 and a locking nut 102. The other end of the phase adjustment shaft 98 is coupled to a phase adjustment knob 104 by means of a worm wheel 106 and a worm gear 108. The worm gear 108 is rotatably supported in a phase adjustment housing 110 by means of a pair of retainer bushings 112 and 114. The worm wheel 106 is rotatably supported inside phase adjustment housing 110 by means of flange bearings 116 and 118. Flange bearing 116 is mounted in a bore (not shown) formed in phase adjustment housing 110. Flange bearing 118 is mounted in a bore formed in a bearing retainer 120. A graduated phase dial 122 is mounted on the bearing retainer 120 to indicate the phase adjustment angle.

Figure 9:
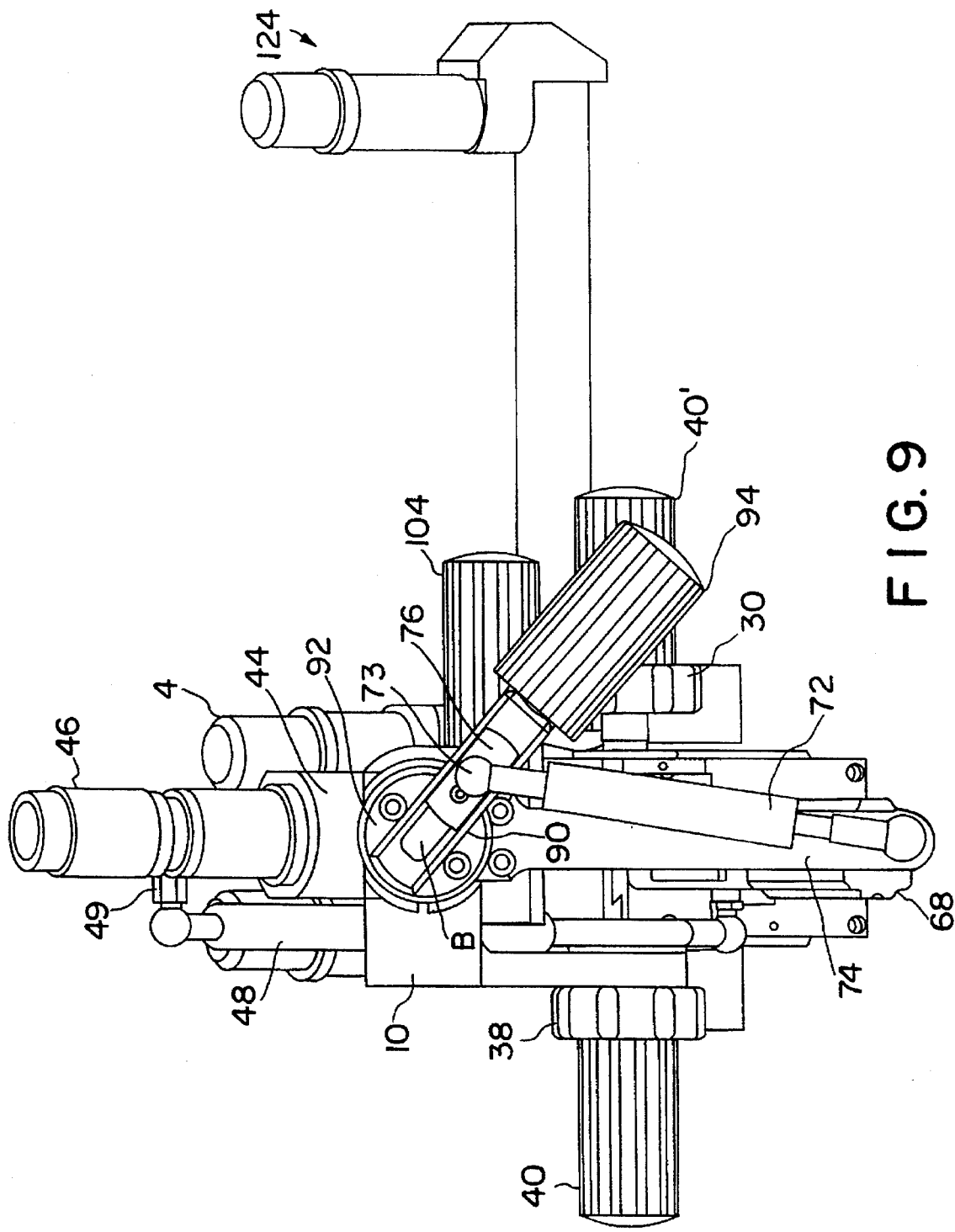
FIG. 9 is a rear elevational view of the microscope assembly shown in FIGS. 1 and 2, with an observer's tube assembly added thereto and with the tip axis counterbalance balanced assembly adjusted to compensate for the moment attributable to the additional weight of the observer's tube assembly.

When the microscope assembly is symmetrically balanced relative to the vertical plane intersecting tip axis B, the upper pivot 73 of gas piston 72 occupies a position coaxial with tip axis B. However, when the microscope assembly is unbalanced, e.g., by attachment of an observer's tube assembly 124 (see FIG. 9) to port 126 on microscope housing 2, the moment caused by the resulting shift in the center of gravity must be counteracted to restore the equilibrium position to the vertical plane through the tip axis B. In accordance with the present invention, this is accomplished using gas piston 72, lower tip axis piston mount 74 and the tip axis counterbalance assembly depicted in FIG. 5. The phase angle is adjusted by rotating phase adjustment knob 104 until the piston slide mount 76 has been rotated by an angle equal to the phase shift of the center of gravity due to the attachment or removal of an accessory. Once the equilibrium position has been restored by this gross torque adjustment, small angular rotations of the microscope assembly about the tip axis and away from the equilibrium position can be counteracted by a fine torque adjustment. Fine torque adjustment is carried out by rotating the tip axis torque adjustment knob 94 to adjust the distance of the upper pivot 73 of tip axis gas piston 72 from the tip axis B, as seen in FIG. 9. As the distance is increased, the tip axis gas piston 72 exerts an increasing moment on the mounting post 42 (via the phase adjustment shaft 98 which is effectively coupled to the mounting post via the worm wheel 106 and the phase adjustment housing 110). The distance is adjusted until the moment developed by piston 72 counterbalances the moment due to the shifting of the microscope assembly center of gravity caused by deviations from the equilibrium position.

Thus, using the microscope balance compensator of the present invention, the balance of the microscope assembly can be maintained throughout the entire operating range for any combination of accessories.

The preferred embodiment of the microscope balance compensator in accordance with the invention has been disclosed for the purpose of illustration. Variations and modifications of the disclosed structure which do not depart from the concept of this invention will be readily apparent to persons skilled in the art of mechanical engineering. For example, springs could be substituted for gas pistons in the respective counterbalance assemblies for the tip and tilt axes. All such variations and modifications are intended to be encompassed by the claims set forth hereinafter.

We claim:

1. A balance compensator for a microscope assembly support system having a first support member having a first axis and a second support member for rotatably supporting said first support member for rotation about said first axis, comprising adjustable counterbalance moment means coupled to said first and second support members for applying a moment to said first support member about said first axis, the magnitude of the moment applied by said adjustable counterbalance moment means being adjustable, wherein said adjustable counterbalance moment means comprises:

a first pivot means supported at a fixed distance from said first axis;

sliding means which are slidable along a second axis perpendicular to said first axis;

sliding support means for slidably supporting said sliding means, said sliding support means extends along said second axis;

a second pivot means fixedly supported on said sliding means;

force producing means for producing a force urging said first and second pivot means in opposite directions; and phase adjustment means for rotating said sliding support means by an angle equal to the change in phase angle due to a shift in the center of gravity of said microscope assembly due to attachment or removal of an accessory.

2. The balance compensator as defined in claim 1, wherein said adjustable counterbalance moment means further comprises means connected to said second support member for supporting said first pivot means, said sliding support means being coupled to said first support member such that said sliding support means is rotatable about said first axis in a first state and is not rotatable about said first axis in a second state, whereby said force producing means applies a moment to said first support member about said first axis when said first pivot means is not coaxial with said first axis.

3. The balance compensator as defined in claim 2, wherein said force producing means comprises a gas piston.

4. The balance compensator as defined in claim 2, wherein said sliding support means comprises a lead screw threadably coupled to said sliding means, a housing configured to prevent rotation of said sliding means in response to rotation of said lead screw and an adjustment knob securely connected to said lead screw.

5. The balance compensator as defined in claim 2, wherein said phase adjustment means comprises:

a phase adjustment tube securely mounted inside a bore formed in said first support member;

a phase adjustment shaft passing through said phase adjustment tube and rotatable relative thereto in said first state, said sliding support means being securely coupled to one end of said phase adjustment shaft; and means for rotating said phase adjustment shaft about said first axis.

6. The balance compensator as defined in claim 5, wherein said phase adjustment shaft rotating means comprises:

a phase adjustment housing securely coupled to one end of said phase adjustment tube;

a worm wheel rotatably supported in said phase adjustment housing;

a worm gear threadably coupled to said worm wheel and rotatably supported in said phase adjustment housing; and an adjustment knob securely connected to said worm gear.

7. The balance compensator as defined in claim 1, wherein said first and second support members are respectively a mounting post supporting a microscope assembly and a coupler rotatably supporting said mounting post.

8. A microscope assembly comprising:

a first mounting post disposed generally vertical and having a first axis;

a coupling means rotatably mounted on said first mounting post for rotation about said first axis;

a second mounting post having a second axis and rotatably mounted on said coupling means for rotation about said second axis;

a support arm having first and second ends, said first end being securely mounted on said second mounting post;

a microscope;

means for supporting said microscope, said microscope supporting means being mounted on said second end of said support arm;

means for coupling an accessory to said microscope; and adjustable counterbalance moment means coupled to said coupling means and to said second mounting post for applying a moment to said second mounting post about said second axis, the magnitude of the moment applied by said adjustable counterbalance moment means about said second axis being adjustable to produce a zero phase shift in response to a shift in the center of gravity of said microscope assembly due to coupling/uncoupling of said accessory.

9. The microscope assembly as defined in claim 8 wherein said adjustable counterbalance moment means comprise:

a first pivot means supported at a fixed distance from said second axis;

sliding means which are slidable along a third axis perpendicular to said second axis;

sliding support means for slidably supporting said sliding means, said sliding support means extends along the third axis, said sliding support means being coupled to said second mounting post such that said sliding support means is rotatable about said second axis in a first state and is not rotatable about said second axis in a second state;

a second pivot means fixedly supported on said sliding means;

force producing means for producing a force urging said first and second pivot means in opposite directions; and phase adjustment means for rotating said sliding support means by an angle equal to the change in phase angle of a torque versus rotation angle function due to a shift in the center of gravity of said microscope assembly upon coupling/uncoupling of said accessory.

10. The microscope assembly as defined in claim 9, wherein said force producing means comprises a gas piston.

11. The microscope assembly as defined in claim 9, wherein said sliding support means comprises a lead screw threadably coupled to said sliding means and a housing configured to prevent rotation of said sliding means in response to rotation of said lead screw, further comprising an adjustment knob securely connected to said lead screw.

12. The microscope assembly as defined in claim 9, wherein said phase adjustment means further comprises:

a phase adjustment tube securely mounted inside a bore formed in said second mounting post;

a phase adjustment shaft passing through said phase adjustment tube and rotatable relative thereto in said first state, said sliding support means being securely coupled to one end of said phase adjustment shaft; and means for rotating said phase adjustment shaft about said second axis.

13. The microscope assembly as defined in claim 12, wherein said phase adjustment shaft rotating means comprises:

a phase adjustment housing securely coupled to one end of said phase adjustment tube;

a worm wheel rotatably supported in said phase adjustment housing;

a worm gear threadably coupled to said worm wheel and rotatably supported in said phase adjustment housing; and an adjustment knob securely connected to said worm gear.

14. A microscope assembly comprising:

a first mounting post disposed generally vertical and having a first axis;

a coupling means rotatably mounted on said first mounting post for rotation about said first axis;

a second mounting post having a second axis and rotatably mounted on said coupling means for rotation about said second axis;

a support arm having first and second ends, said first end being securely mounted on said second mounting post;

a microscope;

means for supporting said microscope on said second end of said support arm in a manner such that said microscope is selectively tiltable about a third axis relative to said support arm; and adjustable counterbalance moment means coupled to said second mounting post and to said microscope supporting means for applying a moment to said microscope supporting means about said third axis, wherein said adjustable counterbalance moment means comprise first and second pivot means, and means for producing a force urging said first and second pivot means in opposite directions.

15. The microscope assembly as defined in claim 14, wherein said adjustable counterbalance moment means further comprise:

first pivot support means for pivotably supporting said first pivot means;

sliding means for sliding between first and second positions along a line perpendicular to said third axis, said first pivot support means being securely connected to said sliding means;

sliding support means for slidably supporting said sliding means during said sliding, said sliding support means being mounted to said microscope supporting means;

second pivot support means for pivotably supporting said second pivot means; and means for securely connecting said second pivot support means to said second mounting post, whereby said force producing means applies a moment to said microscope supporting means about said third axis.

16. The microscope assembly as defined in claim 15, wherein said sliding support means comprises a lead screw threadably coupled to said sliding means and a housing configured to prevent rotation of said sliding means in response to rotation of said lead screw, further comprising an adjustment knob securely connected to said lead screw.

17. The microscope assembly as defined in claim 16, wherein said first pivot means has an axis of rotation which is perpendicular to and does not intersect the axis of rotation of said lead screw.

18. The microscope assembly as defined in claim 14, wherein the magnitude of the moment applied by said adjustable counterbalance moment means about said third axis is adjustable to compensate for a shift in the center of gravity of said microscope assembly due to tilting of said microscope.

19. The microscope assembly as defined in claim 14, further comprising means for attaching an accessory to said microscope, wherein the magnitude of the moment applied by said adjustable counterbalance moment means about said third axis is adjustable to compensate for a shift in the center of gravity of said microscope assembly due to attachment or removal of said accessory.

20. The microscope assembly as defined in claim 14, wherein said force producing means comprises a gas piston.

* * * * *